United States Patent [19]

Graham

[11] Patent Number: 5,385,983
[45] Date of Patent: Jan. 31, 1995

[54] PROCESS FOR PREPARING A WATER-ABSORBENT POLYMER

[75] Inventor: Andrew T. Graham, Midland, Mich.

[73] Assignee: The Dow Chemical Company, Midland, Mich.

[21] Appl. No.: 975,171

[22] Filed: Nov. 12, 1992

[51] Int. Cl.$^6$ ............................................. C08F 8/00
[52] U.S. Cl. ........................... 525/330.1; 525/327.4; 525/327.7; 525/327.8; 525/329.1; 525/329.2; 525/329.4; 525/329.7; 525/330.2; 525/384
[58] Field of Search ............... 525/327.4, 327.7, 327.8, 525/329.1, 329.2, 329.4, 329.7, 330.1, 330.2, 384

[56] References Cited

U.S. PATENT DOCUMENTS

| | | | |
|---|---|---|---|
| 3,897,382 | 7/1975 | Stoy et al. | 524/916 |
| 4,043,952 | 8/1977 | Ganslaw et al. | 524/399 |
| 4,295,987 | 10/1981 | Parks | 525/363 |
| 4,401,797 | 8/1983 | Gallop | 523/106 |
| 4,666,983 | 5/1987 | Tsubakimoto et al. | |
| 4,734,478 | 3/1988 | Tsubakimoto et al. | |
| 4,880,868 | 11/1989 | LeKhac | 524/556 |
| 5,002,986 | 3/1991 | Fujihara et al. | 524/734 |

FOREIGN PATENT DOCUMENTS

| | | |
|---|---|---|
| 0248963 | 6/1986 | European Pat. Off. |
| 0248437 | 6/1987 | European Pat. Off. |
| 3713601 | 11/1981 | Germany |
| 4020780 | 8/1991 | Germany |
| 846321 | 10/1981 | Japan |

*Primary Examiner*—Edward Cain

[57] ABSTRACT

The subject invention provides a process for preparing a water-absorbent polymer by the addition of a surface crosslinking agent to a hydrogel. In particular, the subject invention provides a process for preparing a water-absorbent polymer by the addition of a surface crosslinking agent to a hydrogel in the absence of a surfactant.

14 Claims, No Drawings

PROCESS FOR PREPARING A WATER-ABSORBENT POLYMER

FIELD OF INVENTION

The subject invention pertains to a process for preparing a surface-crosslinked water-absorbent polymer. The subject invention further pertains to a polymer prepared by the inventive process. The subject invention further pertains to a method of using such a polymer.

BACKGROUND OF INVENTION

Water-swellable polymers are used as constituents in personal care devices which absorb bodily fluids, such as sanitary napkins, incontinent devices and disposable baby diapers. Examples of such polymers are disclosed in U.S. Pat. Nos. 3,926,891; 4,190,562; and 4,293,609.

Various processes are known for producing absorbent polymers. For example, U.S. Pat. No. 4,833,222 teaches a process for preparing an absorbent polymer from a neutralized monomer with a surface-active agent. U.S. Pat. No. 4,808,637 teaches the uniform reaction of acrylic acid, an alkali metal salt of carbonic acid, aluminum acetate, sodium sulfate and water, preferably using microwave radiation as a heat source to initiate polymerization.

Another process comprises the steps of preparing a reaction mixture consisting essentially of particular amounts of polymerizable acid group-containing monomers, crosslinking agent and optionally free radical initiator in an aqueous medium and thereafter polymerizing and neutralizing at least a portion of the acid functional groups.

Absorbent polymers used in personal care devices are characterized by certain performance properties, including centrifuge capacity, absorbence under load, shear modulus, and percent extractables.

U.S. Pat. No. 4,666,983 discloses an absorbent article obtained by mixing 100 parts by weight of an absorbent resin powder having a carboxyl group with 0.0001 to 10 parts by weight of a crosslinking agent to crosslink the molecular chains existing at least in the vicinity of the surface of the absorbent resin powder. The patent discloses that at least 70 percent by weight of the particles will preferably pass through a 60-mesh sieve. Comparative Example 2 of the patent provides that when the crosslinking agent was added to a gel-like hydrous polymer having a larger particle size than the powder particles, the effect was contrary to that expected, or was small.

U.S. Pat. No. 4,734,478 discloses a water-absorbing resin powder having the molecular chains crosslinked near the particle surfaces, the resin powder being obtained by mixing 100 parts by weight of a powder of a carboxyl-containing water-absorbing resin with 0.001 to 10 parts by weight of a polyhydric alcohol and heating the mixture at a temperature of at least 100° C. to react the powder with the polyhydric alcohol, the improvement comprising conducting the mixing of the powder and the polyhydric alcohol in the presence of 0.01 to 8 parts by weight of a hydrophilic organic solvent and 0 to 8 parts by weight of water per 100 parts by weight of the powder. The patent provides that not more than 50 percent by weight of the particles of the resin powder will pass through a 200-mesh sieve.

The process incorporated into the product claims of U.S. Pat. No. 4,734,478 suffers the following disadvantages. First, traces of water are quickly absorbed by water absorbent polymers, making it difficult to introduce additives to the polymer particles, which additives are to be applied as an aqueous solution. Second, the addition of an aqueous solution to the polymer powder results in particle agglomeration; when the agglomerated particles are subjected to heat, they may form hard clusters which make additional processing such as breaking and screening necessary. Third, the patent discloses that if the polyalcohols are added without a solvent, good distribution is not possible. The polymer coating formulation therefore preferably contains a hydrophilic organic solvent, e.g., methanol. The use of an organic solvent is not preferred, due to the associated special handling and the solvent recycle/disposal requirements.

U.S. patent application Ser. No. 07/866,628 discloses a process for preparing a surface crosslinked water absorbent polymer, wherein a hydrogel is contacted with a composition containing a polyhydroxy compound and a surfactant to coat the hydrogel. The coated hydrogel is then dried to form particles, is optionally ground to form sized particles, and is heated to crosslink the surface of the particles. In preferred embodiments, the hydrogels will comprise from about 15 to about 100 weight percent polymer, with the remainder comprising water. In preferred embodiment, the hydrogel is preferably in granular form, with particle sizes of about 2 cm or less being more preferred. The composition which contains the polyhydroxy compound and the surfactant will preferably contain from about 0 to about 99 percent water and from about 0 to about 50 weight percent organic solvent. The resultant compositions are disadvantageous to the extent that they require the use of expensive surfactants, which add cost to the finished product.

Japanese Kokai Publication 84632/1981 discloses an absorption agent consisting of a crosslinked poly(alkali metal acrylate) material obtained from 0.01 to 10 parts by weight of a water-soluble and/or water dispersible surfactant and 0.005 to 20 parts by weight of a water-soluble polyvalent alcohol per 100 parts by weight of an acrylic acid/acrylate based polymer composed of from 10–40 mole percent acrylic acid and 60–100 mole percent acrylate salt, wherein the polymer is formed by gel polymerization as a gel which is subsequently heated and dried.

European Patent Application 248,963 discloses a process of post treatment wherein the surface of water-absorbent resin particles are treated with polyquarternary amines to significantly increase the absorption rate and to increase the absorption under load (AUL) by 10 percent. In the disclosed process, the polyquaternary amines are applied as solutions in methanol. A separate blending operation is required to evenly distribute the polyquaternary amine evenly throughout the resin.

European Patent Application 248,437 discloses a process for post surface crosslinking in which an aqueous solution of a water-soluble peroxide radical initiator is sprayed onto the surface of the water absorbent resin particles and the coated particles are heated. The reference alleges the achievement of additional surface crosslinking, leading to a product of improved water absorbency and water absorption rate. The reference discloses that the uniformity of penetration of the aqueous solution into the surface of the absorbent polymer may be improved by using a water soluble organic solvent such as methanol. The disclosed process suffers the disadvantage of using high levels of peroxide free radical initiators, which discolors partly neutralized polyacrylic acid, making the product less appealing for personal care applications. The disclosed process suffers the further disadvantage of increasing the amount of extractable polymer, e.g., low molecular weight water-soluble polymer, if the polymer is subjected to heat.

German Patent DE 3,713,601 discloses a process in which surface crosslinking is obtained by the addition of a crosslinker of glycidyl or polyglycidyl compounds. These crosslinking agents are not preferred in applications wherein the polymer is expected to contact human skin.

In the prior art processes, it has been noted that the contact time of the polymer and the surface crosslinking agent should be sufficient to coat the particles with the surface crosslinking agent, but not so long as to allow diffusion of the surface crosslinking agent into the pores or internal structure of the water-absorbent resin particles. It would be advantageous to provide a process which is flexible with respect to the amount of time for which the polymer may be in contact with the surface crosslinking agent prior to the onset of the surface crosslinking reaction.

Industry would find great advantage in a process for preparing an aqueous fluid absorbent having improved absorbency under load and capacity, which process does not require the use of expensive surfactants and which process does not require the implementation of additional process equipment. Such a process would provide a highly desirable product in a cost-effective manner.

SUMMARY OF INVENTION

Accordingly, the subject invention provides a process for preparing an aqueous fluid absorbent material comprising:

(a) contacting a hydrogel comprising from about 20 to about 95 percent water-absorbent resin bearing carboxyl moieties and from about 5 to about 80 percent water with a composition comprising a surface crosslinking agent in the absence of a surfactant, the composition optionally further comprising additional water and/or a water miscible polar solvent, under conditions such that the surface crosslinking agent coats the hydrogel without substantial penetration into the interior of absorbent resin particles of the hydrogel to form a coated hydrogel;

(b) drying the coated hydrogel, such that the water, and optional additional water and optional solvent if present, are substantially removed and such that the surface crosslinking agent does not significantly react with the carboxyl moieties to form a dried coated resin;

(c) reducing the particle size of the dried coated resin by mechanical means to form dried coated particles; and (d) heating the dried coated particles under conditions such that the surface crosslinking agent reacts with the carboxyl moieties so as to crosslink the surface of the dried coated particles.

DETAILED DESCRIPTION

Generally, water absorbent resin particles are prepared by either a gel polymerization process or by a reverse suspension polymerization process, both of which are well-known. The subject invention is particularly suited to gel polymerization processes.

In gel polymerization processes, monomers are polymerized in aqueous solution. Certain additives, such as crosslinking agents and surfactants, may be incorporated into the monomer mixture. The product of the polymerization process is a hydrogel, which is a water-swollen form of the polymer. Generally, this hydrogel is subjected to mechanical means for reducing the particle size to granulate the hydrogel. Thereafter, the hydrogel is dried to remove the water. The particles are then typically subjected to further mechanical means of particle size reduction and classification including chopping, grinding, and sieving.

Hydrogel, as used herein, means water swollen absorbent resin particles. In preferred embodiments, such hydrogels comprise from about 15 to about 95 percent by weight water absorbent polymer, with the remainder comprising water. In a more preferred embodiment, the hydrogel comprises from about 30 to about 95 percent water absorbent polymer. In a most preferred embodiment, the hydrogel comprises from about 80 to about 95 percent water-absorbent polymer.

Surface crosslinked, as used herein, refers to absorbent resin polymer particles which are contacted with a surface crosslinking agent after completion of polymerization under conditions such that the particles are coated at or near the surface and the particles are exposed to conditions such that the surface crosslinking agent reacts with carboxyl groups at or near the surface of the particle to crosslink the water absorbent resin.

The water-swellable or lightly crosslinked hydrophilic polymers that are usefully used in the present invention can be any of the known hydrophilic polymers which are capable of absorbing large quantities of fluids. In particular, water-absorbent polymers useful in this invention are water-absorbent polymers which contain carboxyl moieties. Preferably, at least about 0.01 equivalent of carboxyl groups are present per 100 grams of the water-absorbent resin.

Among preferred carboxyl-containing water absorbent polymers are hydrolyzates of starch-acrylonitrile graft copolymers, partially neutralized products of starch-acrylic acid graft copolymers, saponification products of vinyl acetate acrylic ester copolymers, hydrolyzates of acrylonitrile copolymers, crosslinked products of hydrolyzates of acrylonitrile copolymers, hydrolyzates of acrylamide copolymers, crosslinked products of hydrolyzates of acrylamide copolymers, partially neutralized products of polyacrylic acids and crosslinked products of partially neutralized polyacrylic acids.

Examples of some suitable polymers and processes for preparing them are disclosed in U.S. Pat. Nos. 3,997,484; 3,926,891; 3,935,099; 4,090,013; 4,093,776; 4,340,706; 4,446,261; 4,683,274; 4,459,396; 4,708,997; 4,076,663; and 4,190,562 herein incorporated by reference. Such hydrophilic polymers are prepared from water-soluble $\alpha,\beta$-ethylenically unsaturated monomers such as monocarboxylic acids, polycarboxylic acids, acrylamide and their derivatives.

Suitable $\alpha,\beta$-ethylenically unsaturated monomers include, for example, acrylic acid, methacrylic acid, crotonic acid, isocrotonic acid and alkali metal salts and ammonium salts thereof; maleic acid, fumaric acid, itaconic acid, acrylamide, methacrylamide and 2-acrylamido-2-methyl-1-propane sulfonic acid and its salts. The preferred monomers include acrylic acid and methacrylic acid and their respective salt forms such as alkali metal or ammonium salts.

The water-soluble monomers useful in the present invention may be used in amounts ranging from about 10 percent to about 80 percent by weight based on the total weight of the aqueous monomer solution. Preferably, the amount ranges from about 20 percent to about 60 percent based on the total weight of the aqueous monomer solution.

Optionally, the minor amounts of other water-soluble, unsaturated monomers, such as alkyl esters of the acid monomers, e.g., methyl acrylate or methyl methacrylate may be present. In addition, certain grafting polymers, such as, for example, polyvinyl alcohol, starch and water soluble or swellable cellulose ethers may be employed to prepare products having superior properties. Such grafting polymers, when employed, are used in amounts up to about 10 weight percent based on the $\alpha,\beta$-ethylenically unsaturated monomer. Further, it may be advantageous to include a chelating agent to remove trace metals from solution, e.g., when a metal reaction vessel is employed. One such chelating agent is VERSENEX V-80 (an aqueous solution of the pentasodium salt of diethylenetriamine pentacetic acid) (Trademark of The Dow Chemical Company). Such chelating agents, when employed, are generally used in amounts between about 100 and about 2000 ppm based on the $\alpha,\beta$-ethylenically unsaturated monomer.

It is desirable to obtain a level of conversion of monomer to polymer of at least about 95 percent conversion. The polymerization may be carried out using acid monomers that are not neutralized or that have been neutralized or partially neutralized prior to the polymerization. Neutralization is conveniently achieved by contacting the aqueous monomer with an amount of basic material sufficient to neutralize between about 20 and about 95 percent of the acid groups present in the acid monomers. Preferably, the amount of basic material will be sufficient to neutralize between about 40 percent and 85 percent, and most preferably between about 55 percent and about 75 percent of the acid groups present in the acid monomers. When pre-neutralizing the monomer solution, it is important to control the neutralization conditions so that the heat of neutralization does not cause the premature polymerization of the monomer mixture. The neutralization is advantageously carried out at temperatures below about 40° C., preferably at temperatures below about 35° C.

Compounds which are useful to neutralize the acid groups of the monomer are typically those which will sufficiently neutralize the acid groups without having a detrimental effect on the polymerization process. Such compounds include alkali metal hydroxides, alkali metal carbonates and bicarbonates. Preferably, the material used to neutralize the monomer is sodium or potassium hydroxide or sodium carbonate or potassium carbonate. In determining the desired degree of neutralization, care must be taken to ensure that the pH of the resulting crosslinked absorbent polymer, which will be contacted with or dispersed in an aqueous fluid to be absorbed, is maintained in a range appropriate for the applications for which the polymer is intended. Alternatively, the polymerization may be carried out employing unneutralized monomers and thereafter neutralizing, as is known in the art.

Conveniently, a conventional vinyl addition polymerization initiator is used in the polymerization of the water-soluble monomers and the crosslinking agent. A free radical polymerization initiator which is sufficiently soluble in the monomer solution to initiate polymerization is preferred. For example, water soluble peroxides such as potassium persulfate, ammonium persulfate, sodium persulfate, and other alkali-metal persulfates, hydrogen peroxide and water soluble azo-compounds such as 2,2'-azobis (2-amidinopropane.HCL) may be used. Some of these initiators, such as hydrogen peroxide can be combined with reducing substances such as sulfites or amines to form known redox type initiators. The amount of initiator used may range from about 0.01 to about 1.0 weight percent, preferably about 0.01 to about 0.5 weight percent, based on the total weight of $\alpha,\beta$-ethylenically unsaturated monomer reactants.

The water-absorbent resin will preferably be lightly crosslinked to render it water-insoluble. The desired crosslinked structure may be obtained by the copolymerization of the selected water-soluble monomer and a crosslinking agent possessing at least two polymerizable double bonds in the molecular unit. The crosslinking agent is present in an amount effective to crosslink the water-soluble polymer. The preferred amount of crosslinking agent is determined by the desired degree of absorption capacity and the desired strength to retain the absorbed fluid. Typically, the crosslinking agent is used in amounts ranging from about 0.0005 to about 5 parts by weight per 100 parts by weight of $\alpha,\beta$-ethylenically unsaturated monomer used. More preferably, the amount ranges from about 0.1 to about 1 part by weight per 100 parts by weight of the $\alpha\beta$-ethylenically unsaturated monomer. If an amount over about 5 parts by weight of crosslinking agent per 100 parts is used, the resulting polymer has too high a crosslinking density and exhibits a reduced absorption capacity and increased strength to retain the absorbed fluid. If the crosslinking agent is used in an amount less than about 0.0005 part by weight per 100 parts, the polymer has too low a crosslinking density, and when contacted with the fluid to be absorbed becomes sticky and exhibits a lower initial absorption rate.

While the crosslinking agent will typically be soluble in the aqueous solution of the $\alpha,\beta$-ethylenically unsaturated monomer, the crosslinking agent may be merely dispersible in such a solution, without negative implications. The use of such dispersing agents is disclosed in U.S. Pat. No. 4,833,222, the relevant portions of which are incorporated herein by reference. Suitable dispersing agents include carboxymethyl cellulose suspending aids, methyl cellulose, hydroxypropyl cellulose, and polyvinyl alcohol. Such dispersing agents are typically provided at a concentration between about 0.005 and about 0.1 weight percent, based on the total weight of $\alpha,\beta$-ethylenically unsaturated monomer reactants.

Preferred crosslinking agents include trimethylolpropanetriacrylate, ethoxylated trimethylolpropanetriacrylate, butyleneglycoldiacrylate, ethyleneglycoldimethacrylate, ethylenebisacrylamide and diallylcarbonate, methylenebisacrylamide, bis(acrylamido)acetic acid and its salts, allyl acrylate, allyl methacrylate and difunctional monovinyl and monoallyl esters and amides. Especially preferred crosslinking agents include methylenebisacrylamide, bis(acrylamido)acetic acid and its salts, allyl acrylate, allyl methacrylate and esters or amides having both a vinyl and an allyl functionality.

In a preferred embodiment for making polymers useful in the practice of this invention, an aqueous solution of the $\alpha,\beta$-ethylenically unsaturated monomer in the partially neutralized form, the crosslinking agent, the initiator and a grafting polymer substrate, if desired, is prepared.

The polymerization of the mixture may be initiated by elevating the temperature of the mixture containing the initiator or by using a redox-type initiator as described above. Generally, the temperature at which polymerization will begin ranges from about 20° C. to about 45° C. The temperature at which the polymerization is carried out is highly dependent on the type of monomers used and the specific initiator system employed. Preferably, the maximum temperature of polymerization ranges from about 50° C. to about 100° C., most preferably from about 60° C. to about 100° C. The method by which the temperature of the polymerization is controlled is not critical so long as sufficient cooling is present to remove the heat which is generated during the polymerization.

The resultant hydrogel typically contains from about 5 to about 65 weight percent water-absorbent polymer and from about 35 to about 95 percent water. The hydrogel is typically initially mechanically sized to form sized hydrogel particles having a reduced size prior to drying. Typically, such sized hydrogel particles have an average diameter less than about 2 cm.

The sized hydrogel particles are typically dried using means well-known in the art. Such drying means include fluidized bed driers, rotary driers, forced air ovens, through circulation band driers, etc. In some instances, drying will occur in two or more stages. In two-stage drying, the sized hydrogel particles are partially dried in the first stage, e.g., the sized hydrogel particles are dried to less than about 15 percent moisture level, preferably about a 10 percent moisture level. During the initial drying, the hydrogel particles tend to fuse together to form a sheet. In two-stage driers, the partially dried hydrogel sheets are broken to form pieces which are very roughty about 10 cm×10 cm×2 cm in dimension. Such pieces are then more fully dried in the second stage, e.g., are dried to a moisture level less than about 5 percent. Following completion of drying, the pieces are more fully sized to form particles having an average diameter less than about 0.8 mm.

The polymer particles are surface crosslinked with a suitable surface crosslinking agent. Such crosslinking agents include polyhydroxyl compounds, polyglycidyl ether compounds, polyfunctional aziridine compounds, polyfunctional amine compounds and polyfunctional isocyanate compounds, with polyhydroxy compounds being especially preferred.

The polyhydroxy compound which is used as a surface crosslinking agent is a compound which contains at least two hydroxyl groups which are capable of readily reacting with the carboxyl groups of the water-absorbent resin of the hydrogel. Suitable polyhydroxy compounds will not volatilize or degrade at the temperature of heating. Preferably, the polyhydroxy compound used in this invention is selected from the group consisting of glycol, diethylene glycol, triethylene glycol, polyethylene glycols, glycerol, polyglycerol, polyethoxylated glycerol, propylene glycol, polypropylene glycols, diethanolamine, triethanolamine, polyethylene oxide, propane diol, butane diol, hydroxy terminated oxyethylene-oxypropylene block copolymers, trimethylolpropane, pentaerythritol, sorbitol, mannitol, sugars, sugar derivatives, polyoxyethylene sorbitol derivatives, polyoxyethylenelanolin derivatives and the like. More preferred polyhydroxy compounds include diethylene glycol, triethylene glycol, glycerol, polyethoxylated glycerol, polyethylene oxide, propylene glycol, trimethylolpropane, pentaerythritol, sorbitol, and polyethylene glycol. An especially preferred polyhydroxy compounds is glycerol.

Specific examples of the polyglycidyl ether compounds are ethylene glycol diglycidyl ether and glycerin diglycidyl ether.

Specific examples of the polyfunctional aziridine compounds are 2,2-bishydroxymethylbutanoltris[3-(1-aziridinyl)propionate], sold under the tradename Chemitite PZ-33; 1,6-hexamethylenediethyleneurea, sold under the tradename Chemitite HZ-22; and diphenylmethanebis-4,4'-N,N'-diethyloneurea, sold under the tradename Chemitite DZ-22, all of which are manufactured by Nippon Shokubai Kagaku Kogyo Co., Ltd.

Specific examples of the polyfunctional amines are ethylenediamine, triethylenetetramine, tetraethylenepentamine, pentaethylenehexamine, and polyethyleneamine.

The polyhydroxy compound which is used as a surface crosslinking agent is a compound which contains at least two hydroxyl groups which are capable of readily reacting with the carboxyl groups of the water-absorbent resin of the hydrogel. Suitable polyhydroxy compounds will not volatilize or degrade at the temperature of heating. Preferably, the polyhydroxy compound used in this invention is selected from the group consisting of glycol, diethylene glycol, triethylene glycol, polyethylene glycols, glycerol, polyglycerol, polyethoxylated glycerol, propylene glycol, polypropylene glycols, diethanolamine, triethanolamine, propane diol, butane diol, hydroxy terminated oxyethylene-oxypropylene block copolymers, trimethylolpropane, pentaerythritol, sorbitol, mannitol, sugars, sugar derivatives, polyoxyethylene sorbitol derivatives, polyoxyethylenelanolin derivatives and the like. More preferred polyhydroxy compounds include diethylene glycol, triethylene glycol, glycerol, polyethoxylated glycerol, polyethylene oxide, propylene glycol, trimethylolpropane, pentaerythritol, sorbitol, and polyethylene glycol. An especially preferred polyhydroxy compounds is glycerol.

The surface crosslinking agent is present in an amount effective to crosslink the surface of the polymer. Such amount is determined by the desired capacity and AUL of the final polymer. Ideally, such amount should significantly improve the gel strength of the polymer, as evidenced by an increased absorption under load (AUL), while not significantly reducing the capacity of the resin. Typically, the surface crosslinking agent is used in amounts ranging from about 0.000025 to about 10 parts by weight of the essentially dried absorbent resin product. More preferably, the amount ranges from about 0.0002 to about 0.005 parts by weight per 1 part by weight of dried absorbent resin product, i.e., from about 200 to about 5000 ppm based on the weight of the dried absorbent resin product. Preferably, the surface crosslinking agent will be provided in an amount of at least about 300 ppm, more preferably at least about 500 ppm, and more preferably at least about 1000 ppm, and most preferably at least about 3000 ppm based on the weight of the dried polymer.

The surface crosslinking agent may be applied to the hydrogel either neat, or in conjunction with water and/or an organic solvent. Preferably, the compositions containing the surface crosslinking agent will contain from about 0 to about 99 percent by weight water, from 0 to 50 percent organic solvent. More preferably, the compositions will contain from about 0 to about 50 percent water, and no organic solvent. Most preferably, the compositions will contain no water and no organic solvent, i.e., the surface crosslinking agent will be applied neat.

The hydrogel and the surface crosslinking agent should be contacted under conditions such that the particles can be coated with the surface crosslinking agent. Preferably, such contacting will be conducted with some form of mechanical distribution, such that adequate distribution of the surface crosslinking agent on the water-absorbent resin particles occurs. Grinding of the resin mass, followed by moderate stirring, shaking, or even a short distance of conveying in a screw-conveyer is sufficient for such adequate distribution of the surface crosslinking agent over the hydrogel particles, particularly if the hydrogel particles are at an elevated temperature. For instance, neat surface crosslinking agent may be applied to the partially dried sized hydrogel particles exiting the first stage of a two-stage drier, whereupon the surface crosslinking agent is distributed over the surfaces of the particles during a mechanical sizing operation that occurs after completion of drying but before heat treatment.

The temperature of contacting can be any temperature at which the surface crosslinking agent does not significantly react with the carboxyl moieties of the absorbent resin polymer. Such temperatures are at least from about 20° to about 150° C. It should be noted that elevated temperatures, i.e., those above ambient temperatures, improve the speed of coating of the hydrogel particles.

Upon application of the surface crosslinking agent, the hydrogel is dried to a moisture level less than about 5 percent. Preferably, the hydrogel is dried to a moisture level from about 1 to about 5 percent. Should the surface crosslinking agent be applied to the hydrogel prior to any drying, e.g., straight from the reactor, the drying will obviously require more time than should the surface crosslinking agent have been applied at some point downstream from the reactor, e.g., after passage through the first stage of a two-stage drier.

The temperature at which the drying takes place is a temperature high enough such that the water and any optional organic solvent is removed in a reasonable time period, yet not so high as to react the surface crosslinking agent with the carboxyl moieties of the water-absorbent resin. Preferably, the temperature of the water-absorbent resin particles during drying is about 170° C. or less. More preferably, the temperature during drying is from about 100° to about 170° C., most preferably from about 150° to about 170° C.

The drying time should be sufficient to remove substantially all of the water and the optional solvent in a reasonable time period, and will depend on the drying system employed. Typically, the drying will reduce the moisture level of the hydrogel to a level from about 1 to about 5 weight percent.

The coated hydrogel will preferably be subjected to mechanical particle reduction means, e.g., chopping, cutting, and/or grinding. Such mechanical particle reduction means serve to reduce the particle size of the water-absorbent resin particles to a particle size acceptable in the ultimate end use. Such mechanical particle reduction will further preferably serve to distribute the surface crosslinking agent over the mechanically reduced particles. Indeed, it has been found that the surface crosslinking agent is dispersed over the surface of the particles after the particles have undergone mechanical particle size reduction, despite the absence of a surfactant. It is for this reason that coating should preceed and heat treatment should follow final sizing.

In a preferred mode, the absorbent resin particles are first chopped, and are then ground. In a preferred embodiment, the resultant particle size is less than about 2 mm, and is more preferably less than about 0.8 mm. Preferably, the resultant particles have a size of at least about 0.02 mm, more preferably at least about 0.05 mm, and most preferably greater than about 0.1 mm.

After drying and particle size reduction, the water-absorbent resin particles are subjected to conditions such that the surface crosslinking agent reacts with the carboxyl moieties of the water absorbent resin, so as to crosslink the water-absorbent resin at or near the surface of the particles. In particular, the dried and coated water-absorbent resin particles are heated for a time sufficient to increase the modulus and/or the absorbency under load. Such heat treatment is preferably carried out at a temperature of at least about 170, more preferably of at least 180, and most preferably of at least about 190° C. Such heat treatment is preferably carried out at a temperature of less than about 250, more preferably less than about 230, and most preferably less than about 210° C.

The time period for heat treatment should be sufficient for the surface crosslinking agent present at or near the surface of the absorbent resin to react with the carboxyl moieties. The exact times of heat treatment required will be affected by the equipment chosen, and can be determined empirically by examination of product properties. Preferably, the time is at least about 3 minutes, and more preferably at least about 5 minutes. If the time is too long, the process becomes uneconomical and a risk is run that the absorbent resin may be damaged. Preferably, the maximum time of heating is about 150 minutes or less, more preferably 60 minutes or less.

The method of heat treatment is not critical. For example, forced air ovens, fluidized bed heaters, heated screw conveyors, and the like may be successfully employed. If desired, the coated and heated polymer may be remoisturized for ease in handling.

The following examples are provided for the purpose of explanation rather than limitation. Unless otherwise indicated, sixty minute 0.3 psi AUL was measured as described in European Patent Application EP 339,461-A1; ninety minute 0.6 psi AUL was measured in the manner described for the measurement of 0.3 psi AUL, except that a 0.6 psi pressure rather than a 0.3 psi pressure was applied and except that the test time was 90 minutes rather than 60 minutes; centrifuge capacity was determined as described in U.S. Pat. No. 4,286,082 except that an absorption time of 30 minutes rather than 3 to 5 minutes was employed; fish eyes formation was determined as described in U.S. Pat. No. 4,666,983; and the extractables and modulus were determined as described in U.S. Pat. No. Re. 32,649, with the relevant portions of each of the cited references being incorporated herein by reference. Further, vortex time was taken as the time for the vortex to disappear when 2 grams of polymer was added to 50 grams of a 0.9 percent saline solution contained in a 100 mL beaker while the saline solution was being stirred with about a ½ to 1 inch vortex on a magnetic mixer. Gel blocking was noted in the vortex rate test if the powdered absorbent resin did not fully disperse into the saline solution. Percent moisture was determined by drying a portion of polymer at 135° C. for about 60 hours, and using the weights before and after drying to calculate the percent moisture of the sample.

EXAMPLE ONE

To a beaker, 300 grams of acrylic acid, 0.75 grams VERSENEX V-80 chelating agent (available from the Dow Chemical Company), 144 grams sodium carbonate, and enough water to bring the final reactor solids to 32 percent were added. To this, 145 grams of a 10 percent aqueous solution of polyvinyl alcohol was added and was thoroughly mixed. Then, 0.63 gram allyl methacrylate was added. The resultant mixture was transferred to a reactor, which was purged with nitrogen to remove air. To the reactor, 4.8 mL of a 10 percent aqueous solution of sodium persulfate and 0.63 mL of a 30 percent aqueous solution of hydrogen peroxide were added. The contents of the reactor were mixed for one to two minutes. Then, 0.6 mL of a 10 percent aqueous solution of sodium erythorbate was added. Polymerization proceeded to completion in about four hours.

The gel was dried in a standard commercial forced air oven. The majority of the particles of the dried resin mass were greater than 0.5 cm in length and breadth. When dry, a portion of the resin mass was ground and screened to pass through a 100 mesh sieve, and was saved as Comparative Example 1-A. The remainder of the unground and unscreened material was treated by weighing portions of the dried resin mass and weighing enough glycerine onto each portion to give the indicated amount of glycerin based on dry solids. Samples of each portion were ground and screened to pass through a 100 mesh sieve, and were heat treated for 35 minutes at 210° C. to form Examples 1A and 1B.

The results of Examples 1A, 1B, and Comparative Example 1-A are set forth in Table One.

EXAMPLE TWO

To a beaker, 300 grams of acrylic acid, 0.75 grams VERSENEX V-80 chelating agent (available from the Dow Chemical Company), 144 grams sodium carbonate, and enough water to bring the final reactor solids to 32 percent were added. To this, 145 grams of a 10 percent aqueous solution of polyvinyl alcohol was added and was thoroughly mixed. Then, 0.63 gram trimethylolpropanetriacrylate was added. The resultant mixture was transferred to a reactor, which was purged with nitrogen to remove air. To the reactor, 4.8 mL of a 10 percent aqueous solution of sodium persulfate and 0.63 mL of a 30 percent aqueous solution of hydrogen peroxide were added. The contents of the reactor were mixed for one to two minutes. Then, 0.6 mL of a 10 percent aqueous solution of sodium erythorbate was added. Polymerization proceeded to completion in about four hours.

The gel was dried in a standard commercial forced air oven. The majority of the particles of the dried resin mass were greater than 0.5 cm in length and breadth. When dry, a portion of the resin mass was screened to be pass through a 100 mesh sieve and was saved as Comparative Example 2-A. The remainder of the unground and unscreened material was treated by weighing portions of the dried resin mass and weighing enough glycerine onto each portion to give the indicated amount of glycerin based on dry solids. Samples of each portion were ground and screened to pass through a 100 mesh sieve, and were heat treated for 35 minutes at 210° C. to form Examples 2A and 2B.

The results of Examples 2A, 2B, and Comparative Examples 2-A and 2-B set forth in Table One.

TABLE ONE

| Sample | Glycerine Concentration (ppm) | Fish Eyes | Vortex Time (sec) | Gel Block | 30 sec capacity (g/g) | 60 sec. capacity (g/g) | 10 min. capacity (g/g) |
| --- | --- | --- | --- | --- | --- | --- | --- |
| Comparative 1-A | 0 | Yes | >200 | Yes | 6.3 | 9.9 | 21.4 |
| 1A | 300 | No | 29 | Yes | 30.1 | 35.1 | 42.2 |
| 1B | 3000 | No | 10 | No | 29.7 | 37.3 | 44.7 |
| Comparative 2-A | 0 | Yes | >200 | Yes | 6.9 | 8.1 | 29.6 |
| 2A | 300 | No | 17 | No | 28.4 | 35.0 | 42.9 |
| 2B | 3000 | No | 11 | No | 29.9 | 37.3 | 42.8 |

Examples One and Two demonstrate that improved absorption rate and reduced fish eye formation and gel blocking can be obtained when a surface crosslinking agent is applied to the dry or partially dry absorbent resin polymer mass prior to grinding. The surface crosslinking agent can be applied in a range of at least from about 300 to about 3000 ppm, based on dry solids.

EXAMPLE THREE

To a reactor, 48 pounds acrylic acid, 53.4 grams allyl methacrylate, 26.5 pounds of an 8 percent aqueous solution of VINOL 523 poly(vinyl alcohol) solution (available from Air Products Corp.), 22 pounds sodium carbonate, 98 pounds water, and 29 grams VERSENEX V-80 chelating agent were added and mixed. To the mixture, 37 grams sodium persulfate in an aqueous solution and 50.8 grams of a 30 percent aqueous solution of hydrogen peroxide were added and mixed. Next, 3.3 grams of sodium erythorbate in an aqueous solution were added. The reactor was then sparged with nitrogen. The polymerization began and was essentially complete in about 2 hours.

The resultant gel was separated into five parts for drying and coating with glycerin. Glycerin was added dropwise to the gel, at the drying stage extrapolated from the indicated percent moisture of the part, in order to give about 500 ppm glycerine, based on the final dried weight of the polymer. When the glycerin was added to the polymer resin mass, samples of the resin mass were taken. Following addition of the glycerin, the samples were dried to a moisture level of 5 percent and were ground and screened. A screen cut between 20 and 140 mesh was taken for use in capacity, AUL, and extractables determinations. A fines cut less than 140 mesh was taken for use in fish eye and vortex time determinations. The samples were heat treated in a commercial forced air oven for 40 minutes at 200° C., resulting in Examples 3A, 3B, 3C, 3D, and 3E. Comparative Example 3-A represents an uncoated, non-heat treated sample of Example 3A. Comparative Example 3-B represents the uncoated sample of Comparative Example 3-A which has been heat treated.

The results of Examples 3A, 3B, 3C, 3D, 3E, and Comparative Examples 3-A and 3-B are set forth in Table Two.

EXAMPLE FOUR

To a reactor, 49 pounds acrylic acid, 37.7 grams trimethylolpropanetriacrylate, a solution of 22.5 pounds sodium carbonate in water, sufficient additional water such that the total amount of water equaled 115 pounds were added and mixed. To the mixture, 15 grams VERSENEX V-80 chelating agent and 103 grams of a 5 percent aqueous solution of polyvinyl alcohol were added and mixed. To the mixture, 38.5 grams of sodium persulfate in an aqueous solution and 40 grams of a 30 percent aqueous solution of hydrogen peroxide were added and mixed. Next, 3.4 grams sodium erythorbate in an aqueous solution were added. The reactor was then sparged with nitrogen. The polymerization began and was essentially complete in about 2 hours.

The resultant gel was separated into five parts for drying and coating with glycerin. Glycerin was added dropwise to the gel, at the drying stage extrapolated from the indicated percent moisture of the sample, in order to give about 500 ppm glycerine, based on the final dried weight of the polymer. At the time the glycerin was added to the polymer resin mass, samples of the resin mass were taken. Following addition of the glycerin, the samples were dried to a moisture level of 5 percent and were ground and screened. A screen cut between 20 and 140 mesh was taken for use in capacity, AUL and extractables determinations. A fines cut less than 140 mesh was taken for use in fish eye and vortex time determinations. The samples were heat treated in a commercial forced air oven for 40 minutes at 200° C., resulting in Examples 4A, 4B, 4C, 4D, and 4E. Comparative Example 4-A represents an uncoated, non-heat treated sample of Example 4A. Comparative Example 4-B represents the uncoated sample of Comparative Example 4-A which has been heat treated.

The results of Examples 4A, 4B, 4C, 4D, 4E, and Comparative Examples 4-A and 4-B are set forth in Table Two.

EXAMPLE FIVE

In a beaker, 300 grams acrylic acid 0.75 grams VERSENEX V-80 chelating agent, 144 grams sodium carbonate, and enough water to bring the final reactor solids to 32 percent were added and mixed. To the mixture, 145 grams of a 10 percent solution of poly(vinyl alcohol) was added and thoroughly mixed. Then, 0.9 grams allyl methacrylate was added, the mixture was added to a reactor, and the reactor was purged with nitrogen. To the reactor, 4.8 mL of a 10 percent aqueous solution of sodium persulfate and 0.63 mL of a 30 percent aqueous solution of hydrogen peroxide were added and mixed for one to two minutes. Then, 0.6 mL of a 10 percent solution of sodium erythorbate were added. The polymerization began and was completed in about 4 hours.

The resultant gel was separated into four parts and was dried in a standard commercial forced air oven. When dry, one portion of the material was ground and saved as Comparative Example 5-1. Other portions of the material were treated by weighing the portions and weighing the indicated amount of glycerin onto the portions. The coated portions were placed in a food blender and were ground and screened to a 20 to 100 mesh cut. The sized and coated portions were placed in a jar and tumbled in a roller mixer for an additional 15 to 30 minutes. The samples were then placed in a forced air oven at 200° C. for 40 minutes to react the glycerin with the carboxyl groups on the absorbent resin. The final products (Examples 5A, 5B, and 5C) and the products of the comparative example were analyzed.

The results of Examples 5A, 5B, 5C, and Comparative Example 5-1 are set forth in Table Three.

TABLE THREE

| Polymer Sample | Glycerine (ppm) | 0.3 psi AUL (g/g) | 0.6 psi AUL (g/g) | Swelling Capacity (g/g) | AUL (0.6) Swelling Cap |
|---|---|---|---|---|---|
| Comparative 5-1 | 0.0 | 10.0 | 9.1 | 36.4 | 0.25 |
| 5A | 286 | 26.2 | 16.3 | 34.0 | 0.479 |
| 5B | 648 | 28.0 | 19.8 | 33.4 | 0.593 |
| 5C | 1031 | 28.6 | 19.7 | 32.8 | 0.600 |

TABLE TWO

| Sample | Percent Moisture | Fish Eyes | Vortex Time (sec) | Capacity (g/g) | 0.3 psi AUL (g/g) | 0.6 psi AUL (g/g) | Percent Extractables |
|---|---|---|---|---|---|---|---|
| Comparative 3-A | 5 | Yes | >150 | 34.0 | 15.5 | 9.6 | |
| Comparative 3-B | 5 | | | 35.3 | 29.2 | 14.3 | 7.66 |
| 3A | 5 | No | 13 | 34.4 | 29.9 | 18.0 | 7.96 |
| 3B | 11.4 | No | 17 | 35.0 | 29.2 | 16.5 | 7.62 |
| 3C | 59.5 | No | 17.5 | 34.6 | 29.8 | 18.1 | 7.64 |
| 3D | 63 | No | 20 | 33.5 | 29.5 | 17.6 | 7.59 |
| 3E | 202.5 | No | 17.5 | 34.1 | 30.0 | 18.3 | 7.64 |
| Comparative 4-A | 6.92 | Yes | >150 | 44.3 | 7.9 | 8.4 | 17.59 |
| Comparative 4-B | 6.92 | | | 32.9 | 23.0 | 11.6 | 12.10 |
| 4A | 6.92 | No | 15 | 30.9 | 25.1 | 16.9 | 12.39 |
| 4B | 13.38 | No | 25 | 32.2 | 22.9 | 12.0 | 12.84 |
| 4C | 37.4 | No | 24 | 31.3 | 24.0 | 13.4 | 12.08 |
| 4D | 80.4 | No | 29 | 31.8 | 24.2 | 12.9 | 11.38 |
| 4E | 208 | No | 27 | 33.4 | 22.5 | 10.9 | 11.91 |

Examples Three and Four demonstrate that the surface crosslinking agent may be applied to gel, wherein the gel comprises between about 30 and about 95 percent polymer. Thus, the surface crosslinking agent may be directly added to the hydrogel prior to drying, without sacrificing polymer performance.

The difference between Comparative Examples 5-1 and 5-2 is typical of the way in which absorbent polymers made under these conditions react to heating. See U.S. Ser. No. 756,731. The effects of the surface treatment are found by comparing the results of Examples 5A through 5C. Some reduction in centrifuged capacity was observed. However, a slight increase in 0.3 psi AUL and a substantial increase in 0.6 psi AUL likewise resulted. The improvement as a result of the present invention can be seen in the improvement in AUL/-Swelling capacity in the rightmost column of Table Three.

EXAMPLE SIX

Polymerizations were carried out in the same manner as described in Example 5, excepting that the glycerin was replaced with the indicated coating material. Table Four lists the coating material, the account of coating material used, and the product properties after heat treatment. Examples 6A, 6B, 6C, 6D and 6E are examples of the invention. Comparative examples 6-A1, 6-B1, 6-B2, 6-B3, and 6-B4 correspond to examples 6A, 6B, 6C, 6D and 6E, excepting that the comparative examples represent uncoated samples which have not been heat treated. Comparative examples 6-A2, 6-B2, 6-C2, 6-D2, and 6-E2 correspond to examples 6A, 6B, 6C, 6D and 6E, excepting that the comparative examples represent uncoated samples which have been heat treated in the manner for heat treating the samples of Examples 6A, 6B, 6C, 6D and 6E. The final products (Examples 6A, 6B, 6C, 6D and 6E) and the products of the comparative examples were analyzed.

The results of Examples 6A, 6B, 6C, 6D, 6E, of Comparative Examples 6-A1, 6-A2, 6-A3, 6-A4, 6-A5, and of Comparative Examples 6-B1, 6-B2, 6-B3, 6-B4, and 6-B5 are set forth in Table Four.

bonate, and enough water to bring the final reactor solids to 32 percent were added and mixed. To the reactor, the desired crosslinking agent was added. In the case of Example Seven, 0.95 grams methylenebisacrylamide crosslinking agent was added, the mixture was added to a reactor, and the reactor was purged with nitrogen. In the case of Example Eight, 0.95 grams allyl methacrylate crosslinking agent was added, the mixture was added to a reactor, and the reactor was purged with nitrogen.

To the reactor, 4.8 mL of a 10 percent solution of sodium persulfate and 0.63 grams of a 30 percent solution of hydrogen peroxide were added and mixed for one to two minutes. Then, 0.6 grams of a 10 percent solution of sodium erythorbate were added. The polymerization began and was completed in about 4 hours.

The resultant gels were each separated into two parts and were dried in a standard commercial forced air oven. When dry, one portion of each material was ground and saved as Comparative Examples 7-1, 7-2, 8-1 and 8-2. Other portions of the material were treated by weighing the portions and weighing the indicated amount of the surface crosslinking agent onto the portions. The coated portions were placed in a food blender and were ground and screened to a 20 to 100 mesh cut. The sized products were coated with the indicated amount of coating material and were placed in a jar and tumbled in a roller mixer for an additional 15 to 30 minutes. The samples were then placed in a forced air oven at 200° C. for 40 minutes to react the hydroxyl groups of the coating materials with the carboxyl

TABLE FOUR

| Coating Sample | Chemical | Coating (ppm) | 0.3 psi AUL (g/g) | 0.3 psi AUL (g/g) | Swelling Capacity (g/g) | Modulus (dynes/cm$^2$) | 0.6 psi AUL Capacity |
|---|---|---|---|---|---|---|---|
| Comparative 6-A1 | polyethylene | 0.0 | 13.6 | 9.0 | 33.1 | 22100 | 0.27 |
| Comparative 6-A2 | oxide | 0.0 | 29.5 | 19.0 | 32.9 | 38300 | 0.57 |
| 6A | (avg. mol. wt = 200) | 997 | 29.7 | 23.5 | 32.2 | 38700 | 0.72 |
| Comparative 6-B1 | polyethoxyalated | 0.0 | 9.9 | 8.5 | 35.4 | 22000 | 0.24 |
| Comparative 6-B2 | glycerol | 0.0 | 26.2 | 12.2 | 34.8 | 31500 | 0.35 |
| 6B | (avg .mol. wt = 212) | 995 | 27.5 | 18.5 | 33.3 | 34200 | 0.55 |
| Comparative 6-C1 | propylene glycol | 0.0 | 12.0 | 8.9 | 35.3 | 20200 | 0.25 |
| Comparative 6-C2 |  | 0.0 | 23.8 | 12.1 | 34.5 | 28200 | 0.35 |
| 6C |  | 1035 | 29.4 | 17.4 | 33.1 | 33800 | 0.52 |
| Comparative 6-D1 | polyethylene | 0.0 | 10.5 | 8.7 | 34.9 | 21300 | 0.25 |
| Comparative 6-D2 | glycol | 0.0 | 26.6 | 13.5 | 33.9 | 34500 | 0.40 |
| 6D | (avg. mol. wt. = 600) | 1991 | 26.7 | 16.4 | 33.8 | 34600 | 0.49 |
| Comparative 6-E1 | Sorbitol | 0.0 | 16.9 | 9.1 | 32.9 |  | 0.28 |
| Comparative 6-E2 | (50% aqueous | 0.0 | 29.6 | 14.6 | 33.6 |  | 0.43 |
| 6E | solution) | 501 | 29.8 | 18.5 | 33.5 |  | 0.55 |

The data set forth in Table Four illustrates that any polyfunctional alcohol containing material would be expected to perform satisfactorily in the process of the present invention.

EXAMPLES SEVEN AND EIGHT

In a beaker, 300 grams acrylic acid 0.75 grams VERSENEX V-80 chelating agent, 144 grams sodium cargroups on the absorbent resin. The final products (Examples 7A, 7B, 7C, 7D, 8A, 8B, 8C, and 8D) and the products of the comparative examples (7-1, 7-2, 8-1, and 8-2) were analyzed.

The results of Examples 7A, 7B, 7C, 7D, 8A, 8B, 8C, and 8D and comparative examples 7-1, 7-2, 8-1, and 8-2 are set forth in Table Five.

TABLE FIVE

| Sample | Coating Chemical | Coating ppm | AUL g/g 0.3 psi | AUL g/g 0.6 psi | Swelling Capacity g/g |
|---|---|---|---|---|---|
| Comparative 7-1 |  | 0 | 27.9 | 16.5 | 27.4 |
| 7A | Glycerine | 533 | 30.0 | 26.7 | 29.6 |
| Comparative 7-2 |  | 0 | 27.9 | 17.7 | 26.7 |
| 7B | polyethylene oxide (avg. mol. wt. = 200) | 587 | 31.0 | 25.3 | 30.0 |
| 7C | Diethylene glycol | 519 | 30.9 | 25.6 | 30.2 |
| 7D | polyethoxylated | 542 | 31.2 | 25.9 | 30.1 |

TABLE FIVE-continued

| Sample | Coating Chemical | Coating ppm | AUL g/g 0.3 psi | AUL g/g 0.6 psi | Swelling Capacity g/g |
|---|---|---|---|---|---|
| | glycerol (avg. mol. wt. = 212) | | | | |
| Comparative 8-1 | | 0 | 27.0 | 14.4 | 27.5 |
| 8A | Glycerine | 505 | 30.3 | 26.3 | 29.1 |
| Comparative 8-2 | | 0 | 26.8 | 18.9 | 26.3 |
| 8B | polyethylene oxide (avg. mol. wt. = 200) | 536 | 29.9 | 24.0 | 28.9 |
| 8C | Diethylene glycol | 520 | 29.5 | 23.8 | 28.9 |
| 8D | polyethoxylated glycerol (avg. mol. wt. = 212) | 522 | 29.5 | 24.2 | 28.8 |

The data set forth in Table Five illustrates that polymers of the subject invention which are free of poly(vinyl alcohol) which utilize allyl methacrylate and/or methylenebisacrylamide type crosslinking agents, result in polymers having very desirable absorptive properties.

EXAMPLE NINE

Polymerizations were conducted in the same manner as described with respect to Example 5, except that the coating material was a mixture of glycerine and water as shown in Table Six to make absorbent resins 9A, 9B, and 9C. Comparative Example 9-1 is a heat treated uncoated sample.

The results of Examples 9A, 9B, 9C and comparative example 9-1 are set forth in Table Six.

TABLE SIX

| Sample | Coating Composition | Coating (ppm) | 0.3 psi AUL (g/g) | 0.6 psi AUL (g/g) | Swelling Capacity (g/g) |
|---|---|---|---|---|---|
| Comparative 9-1 | | 0.0 | 23.9 | 12.2 | 36.8 |
| Comparative 9A | 80% Glycerine | 514 | 26.6 | 16.9 | 34.2 |
| Comparative 9B | 65% Glycerine | 501 | 27.2 | 19.2 | 34.0 |
| Comparative 9C | 50% Glycerine | 500 | 27.2 | 16.7 | 34.8 |

The data set forth in Table Six illustrates that while the presence of water as a solvent for the coating material is not necessarily beneficial, at the levels indicated here, it does not harm the spread of the coating chemical over the surface of the absorbent resin. Despite the presence of water, the improved combination of swelling capacity and AUL of the present invention is observed.

What is claimed is:

1. A process for preparing an aqueous fluid absorbent material comprising the following sequential steps:
   (a) contacting a hydrogel comprising from about 20 to about 95 percent water-absorbent resin bearing carboxyl moieties and from about 5 to about 80 percent water with a surface crosslinking composition comprising an organic surface crosslinking agent in the absence of a surfactant, the surface crosslinking composition optionally further comprising additional water and/or a water miscible polar solvent, under conditions such that the organic surface crosslinking agent coats the hydrogel without substantial penetration into the interior of absorbent resin particles of the hydrogel to form a coated hydrogel;
   (b) drying the coated hydrogel, such that the water, and optional additional water and optional solvent if present, are substantially removed and such that the organic surface crosslinking agent does not significantly react with the carboxyl moieties to form a dried coated resin;
   (c) reducing the particle size of the dried coated resin by mechanical means to form dried coated particles; and
   (d) heating the dried coated particles under conditions such that the organic surface crosslinking agent reacts with the carboxyl moieties so as to crosslink the surface of the dried coated particles.

2. The process of claim 1, wherein the drying of step (b) results in a dried coated resin having a water content less than about 10 percent.

3. The process of claim 1, wherein the drying of step (b) occurs at a temperature from about 100° to about 175° C.

4. The process of claim 1, wherein the reducing of step (c) results in dried coated particles having an average particle diameter less than about 0.8 mm.

5. The process of claim 1, wherein the heating occurs at a temperature from about 175° to about 210° C. for from about 5 to about 75 minutes.

6. The process of claim 1, wherein the hydrogel has a water content less than about 10 weight percent.

7. The process of claim 1, wherein the organic surface crosslinking agent is a polyhydroxy compound.

8. The process of claim 1, wherein the organic surface crosslinking agent is glycerol.

9. The process of claim 1, wherein the organic surface crosslinking agent is provided at a level of at least about 200 ppm based on the weight of the water-absorbent resin.

10. The process of claim 1, wherein the organic surface crosslinking agent is provided at a level of at least about 500 ppm based on the weight of the water-absorbent resin.

11. The process of claim 1, wherein the organic surface crosslinking agent is provided at a level of at least about 1000 ppm based on the weight of the water-absorbent resin.

12. The process of claim 1, wherein the organic surface crosslinking agent is provided at a level of at least about 3000 ppm based on the weight of the water-absorbent resin.

13. The process of claim 1, wherein the surface crosslinking composition comprises from about 50 to about 100 percent organic surface crosslinking agent and from about 0 to about 50 percent water, the composition being free from organic solvent.

14. A method for using the aqueous fluid absorbent material of claim 9 comprising incorporating the absorbent material into a personal care device.

* * * * *